United States Patent
Fabre et al.

(10) Patent No.: US 8,900,842 B2
(45) Date of Patent: Dec. 2, 2014

(54) METHOD OF STORING AND/OR TRANSPORTING IN VITRO CELL CULTURES

(75) Inventors: Myriam Fabre, Barcelona (ES); Sonia Gonzalez Menoyo, Barcelona (ES); Mariana Lopez Matas, Barcelona (ES); Roser Pagan I Esquius, Barcelona (ES)

(73) Assignee: Advanced In Vitro Cell Technologies, S.L., Barcelona (ES)

( * ) Notice: Subject to any disclaimer, the term of this patent is extended or adjusted under 35 U.S.C. 154(b) by 2528 days.

(21) Appl. No.: 10/563,033

(22) PCT Filed: Mar. 29, 2004
(Under 37 CFR 1.47)

(86) PCT No.: PCT/ES2004/000140
§ 371 (c)(1),
(2), (4) Date: Jan. 2, 2007

(87) PCT Pub. No.: WO2005/003331
PCT Pub. Date: Jan. 13, 2005

(65) Prior Publication Data
US 2009/0239282 A1 Sep. 24, 2009

(30) Foreign Application Priority Data
Jul. 1, 2003 (ES) .................................. 200301526

(51) Int. Cl.
C12M 1/00 (2006.01)
C12N 11/00 (2006.01)
C12N 11/02 (2006.01)
C12N 11/16 (2006.01)
C12N 5/00 (2006.01)

(52) U.S. Cl.
CPC .......... *C12N 5/0068* (2013.01); *C12N 2533/50* (2013.01); *Y10S 435/975* (2013.01)
USPC ......... 435/174; 435/177; 435/307.1; 435/975

(58) Field of Classification Search
CPC ........... C12Q 1/6869; C12Q 2565/629; C12Q 2525/186; C12Q 2527/125; C12Q 2535/101; C12Q 2563/173; B01F 13/0059; B01J 2219/00317; B01J 2219/00459; B01J 2219/00468; B01L 2200/0668; B01L 2400/0409; B01L 2400/0415; B01L 2400/043
See application file for complete search history.

(56) References Cited

U.S. PATENT DOCUMENTS 6,194,138 B1 2/2001 Zander

FOREIGN PATENT DOCUMENTS

| EP | 0702081 A2 | 3/1996 |
| EP | 1127580 A2 | 8/2001 |
| WO | WO-01/66783 A1 | 9/2001 |
| WO | WO-02/074301 A1 | 9/2002 |

OTHER PUBLICATIONS

Gómez-Lechón, Maria J., et al., Expression and induction of a large set of drug-metabolizing enzymes by the highly differentiated human hepatoma cell Ii, Eur. J. Biochem., 2001, pp. 1448-1459, vol. 268.
Irvine, Jennifer D., et al., MDCK (Madin-Darby canine kidney) cells: A tool for membrane permeability screening, J. Pharm. Sci., Jan. 1999, pp. 28-33, vol. 88, No. 1.
Jaap Gaillard, Pieter, et al., Establishment and functional characterization of an in vitro model of the blood-brain barrier, comprising a co-culture o, Eur. J. Pharm. Sci., Jan. 2001, pp. 215-222, vol. 12, No. 3.
Le Ferrec, Eric, et al., In Vitro Models of the Intestinal Barrier, ATLA, Nov./Dec. 1999, pp. 649-668, vol. 29, No. 6.
Rubas, W. et al., Flux measurements across Caco-2 monolayers may predict transport in human large intestinal tissue, J. Pharm. Sci., Feb. 1996, pp. 165-169, vol. 85, No. 2.
Vailhé, Bruno, et al., In Vitro Models of Vasculogenesis and Angiogenesis, Lab Invest., Apr. 2001, pp. 439-452, vol. 81, No. 4.
Walter, Elke, et al., HT29-MTX/Caco-2 cocultures as an in vitro model for the intestinal epithelium: In vitro-in vivo correlation with permeab, J. Pharm. Sci., Oct. 1996, pp. 1070-1076, vol. 85, No. 10.

*Primary Examiner* — Debbie K Ware
(74) *Attorney, Agent, or Firm* — Hultquist, PLLC; Steven J. Hultquist

(57) ABSTRACT

The invention relates to a method of storing and/or transporting in vitro two-dimensional cell cultures. The inventive method comprises the following steps consisting in: a) coating a cell culture that is immobilized on an asymmetric support with a gelatine solution in culture medium at a concentration of between 1 and 5%; b) solidifying the gelatine added to the support at a temperature of between 15 and 25° C.; and c) storing and/or transporting the cell culture at a temperature of between 15 and 25° C. for a period of up to 96 hours. The invention also relates to a kit which is used to store and/or transport the in vitro two-dimensional cell cultures according to the inventive method, said kit comprising: i) an asymmetric support, and (ii) a gelatine solution in culture medium at a concentration of between 1 and 5%.

12 Claims, 1 Drawing Sheet

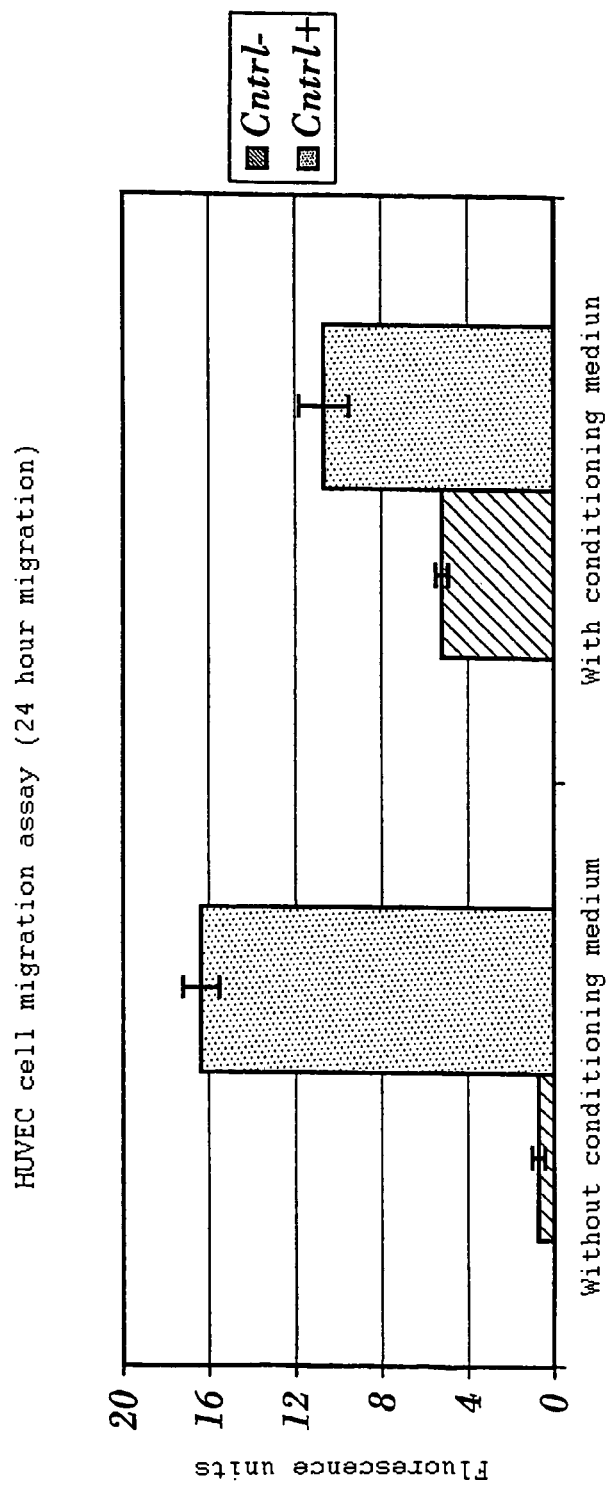

METHOD OF STORING AND/OR TRANSPORTING IN VITRO CELL CULTURES

CROSS-REFERENCE TO RELATED APPLICATIONS

This application is filed under the provisions of 35 U.S.C. §371 and claims the priority of International Patent Application No. PCT/ES2004/000140 filed Mar. 29, 2004, which in turn claims priority of Spanish Patent Application No. 200301526 filed Jul. 1, 2003. The disclosures of said International Patent Application and Spanish Patent Application are hereby incorporated herein by reference, in their respective entireties, for all purposes.

FIELD OF THE INVENTION

The invention relates to obtaining a method of storing and/or transporting in vitro two-dimensional cell cultures, as well as to producing a kit to store and/or transport said cultures.

BACKGROUND OF THE INVENTION

Cell cultures, whether homogeneous or not (cocultures), may be useful models for some genetic, biochemical, metabolic or physiological processes that take place within the living organism. Their ease of use allows a large number of conditions to be analysed before performing the definitive experiments on animals or clinical tests on human beings. In vitro models are a tool for validating new therapeutic targets, to select seeds in high-performance systems, to define the mechanism of action of new molecules and, in general, for biomedical, biotechnological or cosmetic research.

In general, all models based on cell cultures have a limited useful life. Thus, culture cells pass through different differentiation phases, and require continuous manipulation to maintain the properties that make them a suitable model. For example, the gastrointestinal barrier model based on the confluent culture of Caco-2 cells requires 21 days to reach the state of differentiation which allows many of the properties of intestinal mucous to be reproduced (Le Ferrec et al., ATLA 29:649-668, 1999), and its use is prolonged only during a window of approximately 3 to 5 days. BC2 cells, used as a model of hepatic cell, require between three and four weeks of differentiation before they acquire the properties that make them a good model, and the subsequent culture conditions are essential for them to respond to the experimental treatments in a similar way to hepatocytes (M J Gómez Lechón et al., Eur. J. Biochem. 268:1448, 2001). Huvec umbilical cord cells, grown to confluence, may be induced to form structures comparable to blood veins in suitable experimental conditions, for which reason they constitute a good model of angiogenesis (Vailhe et al., Lab. Invest. 81:439-452, 2001), Nevertheless, the number of cell divisions prior to the experiment and the stimulus used are critical to obtaining a suitable response.

These limitations in the manipulation and generation of the different in vitro cell models make them difficult to implement for occasional users, and in general limit the marketing of the models in their end format. The problem gets worse in complex models, wherein the cells should imitate the organism's natural barriers (Rubas et al., J. Pharma. Sci., 85:165-169, 1996; Walter et al., J. Pharma Sci., 85:1070-1076; Irvine et al., J. Pharma Sci., 88:28-33, 1999; Gaillard et al., Eur. J. of Pharma Sci., 12:215-222, 2001); or the cultures should be performed on asymmetric supports, separating two compartments or with a strong dependence on the polarisation of the system components. In these cases, to the complexity of the model and its time limits, we can add mechanical-type problems, which mean bumps or shaking may invalidate the system. Researchers can access the different model components (support, culture medium and additives and cell lines) and later they should combine them in the laboratory using more or less laborious processes). In the best of the cases, the final researcher may receive the cells ready-for-use, but with limitations which practically mean it is obligatory to perform the experiments within two days after their reception, and they impose serious restrictions on the distribution of the model by the company marketing it, such as, for example, In Vitro Technologies. Document EP 702 081 discloses a method for the storage and transport of three-dimensional tissues which consists of positioning said three-dimensional tissue fixed on two types of sponges in a gelatine solution, so that this gels with cooling, thus making it easier to transport and store.

Therefore, there is an existing need in the state of the art for providing a method to be able to supply models based on ready-to-use organized two-dimensional cell cultures and with their functional properties intact so that, on the one hand, the researcher has a margin of manoeuvre for its use and, on the other, the supplying company may consider delivery times within the reasonable logistic margins of international distribution.

The object of the present invention consists of providing a method of storing and transporting in vitro organized two-dimensional cell cultures which resolves the aforementioned needs of the state of the art.

BRIEF DESCRIPTION OF THE FIGURES

FIG. 1. Response in a HUVEC endothelial cell migration assay, either stimulated or not, without conditioning medium (cells which have not been kept in the medium with gelatine) and with conditioning medium (72 hours after having been maintained in the medium with gelatine), measured in fluorescence units.

DESCRIPTION OF THE INVENTION

In its main aspect, the invention provides a method of storing and/or transporting in vitro organized cell cultures which comprises the following steps:
a) coating an organized cell culture that is immobilised on an asymmetric support with a gelatine solution in the culture medium at a concentration of between 1 and 5%, said cell culture comprising cells in suitable functional state,
b) solidifying the gelatine added to the support at a temperature of between 15 and 25° C., and
c) storing and/or transporting the cell culture at a temperature of between 15 and 25° C. for a period of up to 96 hours.

In a second aspect, the present application also provides a kit for storing and/or transporting the in vitro two-dimensional cell cultures according to the method of the invention which comprises:
(i) an asymmetric support, and
(ii) a gelatine solution in the culture medium at a concentration of between 1 and 5%.

DETAILED DESCRIPTION OF THE INVENTION

In its main aspect, the invention provides a method of storing and/or transporting in vitro organized two-dimensional cell cultures which comprises the following steps:

a) coating an organized cell culture that is immobilised on an asymmetric support with a gelatine solution in the culture medium at a concentration of between 1 and 5%, said cell culture comprising cells in suitable functional state, b) solidifying the gelatine added to the support at a temperature of between 15 and 25° C., and c) storing and/or transporting the cell culture at a temperature of between 15 and 25° C. for a period of up to 96 hours.

In a particular embodiment, the method of the invention comprises the following additional steps:

d) liquefication of the gelatine, e) elimination of the gelatine and substitution of same by a culture medium, and f) incubation of the culture.

The method of the invention makes it possible for the physiological properties of the cells to be maintained during the storage and/or transport of the cell culture or model and, furthermore, the essential mechanical properties for the cell model are protected.

Within the context of the present invention, asymmetric support is understood to be those receptacles which contain two compartments physically separated by a semi-permeable membrane whereon the culture cells are positioned. As preferred asymmetric support, the present invention uses the transwell-type support.

The two-dimensional cell cultures of the invention are organised cultures such as, for example: Huvec cells, grown to confluence on a collagen support; confluent culture of differentiated Caco-2 cells; or any other type of cells capable of growing in monolayers such as fibroblasts, tumoral, hepatic, endothelial cells, etc. Thus, examples of intestinal epithelial lines derived from tumours are Caco-2, TC7, HT29 M6; an example of kidney epithelial line is MDCK; an example of primary human skin keratinocytes is HEK; finally, examples of primary endothelial lines or cultures are HUVEC, HMEC-1, BBEC, HAEC and BAEC. Preferably, the organised two-dimensional cell culture of the invention is differentiated, polarised and is functionally active.

According to the present invention, the gelatine solution is prepared by dissolving gelatine in the same culture medium, which acts as solvent. Thanks to the use of the culture medium as solvent, the culture medium stored and/or transported culture according to the method of the present invention guarantees the user that the culture's functional properties will be preserved and its immediate use. Preferably, the gelatine solution used is 2.5% by weight.

In the method of the invention any commercial gelatine can be used, such as, for example type A pigskin gelatine. Similarly, any commercial culture medium can be used, such as, for example, DMEM (1 g/L, glucose). It is "advisable" to prepare the gelatine solution a maximum of 7 days prior to applying it to the culture, otherwise, it loses part of its "preservation" properties, which are necessary for the correct functioning of the present invention.

The gelatine solution in the culture medium can be supplemented with foetal bovine serum (10% FBS) and Penicillin/Steptomycin/L-Glutamine (complete culture medium).

The cell culture can be prepared in the following form: firstly, performing a coating before inoculating the cells, which involves: a) positioning the inserts or transwells on the corresponding sized wells; 2) applying a collagen solution (or another extracellular matrix component, depending on the cell type) to the upper face of the filters (semi-permeable membranes) of each insert in DMEM culture medium (1 g/L glucose) without serum (or another commercial medium); and 3) preferably leave at 37° C. in the cell cultures stove (90% humidity, 5% $CO_2$). Before using the insert, the excess coating solution is drawn up from the apical face, it is left approximately during 15 to 30 minutes in the culture stove, and the cells corresponding to the determined density for each cell type and for each assay type are seeded. The culture is maintained for the necessary time within the scope of the functional state of the system, preferably changing the medium every 48-72 hours if necessary. The characteristics of the inserts or transwells used (size, pore diameter, material) are specifically determined by the cell type and the assay to which the present invention can be applied. In accordance with the cell type used in the culture and the assay type, controls are performed to determine the functional state of the cell system after a number of days elapsed. For example, in the case of cell systems which are used as barrier models, TEER (Trans Epithelial Electric Resistance) and paracellular permeability measurements can be used. In the case of cells systems which are used for invasion/migration assays, the migration/invasion capacity is determined by marking with a fluorochrome (e.g. calcein) the cells which have migrated to the lower part of the filter and subsequent quantification by fluorimetry.

According to the present invention, the cell culture is coated with a gelatine solution in the culture medium at a concentration of between 1 and 5%. In general terms, the gelatine will be applied at the precise moment when it has been checked that the cell system has just reached the suitable functional state, so that the already functional cell system is immobilised, but the user has a time margin to perform their assays when the system is received. The elapsed culture time is called "lifetime". From here, the application of the present invention to ready-to-use cell systems. The lifetimes of the cell culture, i.e. the lifetime of the culture wherein the gelatine is applied, do not only depend on the culture cell types (fibroblasts, tumoral line, etc.) but also on its functional application (barrier permeability assay, adhesion assay, migration assay, invasion assay). Its determination is a question of experimental practice. Thus, in the specific case of the fibroblasts and HUVEC cells inoculated in transwell-type supports and in conditions wherein these cells are functionally active for a migration assay, the lifetime will be between 30 minutes and 1 hour after inoculating the cells. In the case of an invasion assay, the time will be between 1 and 24 hours. In contrast, in the case of Caco-2 cells inoculated in transwells, the lifetime will be 13 days after inoculating the cells, a time after which they are already functional as a barrier and the gelatine is applied, leaving the user up to day 25 of growth to perform the barrier permeability test.

In the context of the present invention, suitable functional state is understood to be the state the viable cell cultures present when they are capable of performing the function they have been assigned in the assay.

To apply the gelatine to the culture, it is firstly necessary to completely liquefy the gelatine solution and equilibrate it to the culture medium temperature, generally at 37° C. Then, the culture medium is removed from the two compartments of each insert and the culture is washed with culture medium in the 2 compartments of each insert. Then, 2.5% liquid gelatine is applied in the apical compartment and the basal compartment, and it is left to solidify for between 2 to 3 hours in the flow hood at room temperature (20-25° C.). Once the gelatine has solidified, the plates are sealed with parafilm and they are kept at room temperature until they are used (maximum of 4 days later).

When one wants to use the immobilised culture, the plate is incubated with solid gelatine within a cell incubator until the complete liquefication of the gelatine, preferably at 37° C., 90% humidity and 4% $CO_2$ for 3 to 4 hours until the gelatine is completely liquefied. Then, the culture is removed from both compartments by suction and the culture is washed with equilibrated culture medium at 37° C. Next, the specific culture medium for the cells in question is applied and they are preferably incubated at 37° C., in 90% humidity and 5% $CO_2$ until its use.

In a second aspect, the invention provides a kit for storing and/or transporting the in vitro organized two-dimensional cell cultures according to the method of the invention, said kit comprising:
(i) an asymmetric support, and
(ii) a gelatine solution in the culture medium at a concentration of between 1 and 5%.

In a particular embodiment; the kit of the present invention uses a transwell-type support as asymmetric support.

The examples described below serve to illustrate the invention.

EXAMPLES

Example 1

Method of Storing and/or Transporting the In Vitro Caco-2 Intestinal Barrier Model 1—Gelatine Preparation Type A pigskin gelatine is used, dissolved in DMEM culture medium (1 g/L glucose) at 50° C., directly at the use concentration (maximum concentration that can be dissolved: 10%). In the present case, 2.5 g of powdered gelatine are weighed and dissolved with 100 ml of DMEM culture medium (1 g/L glucose). It is immediately sterilised (with "heat") by filtration through 0.22 •m pore filters. It is then supplemented with foetal bovine serum (10% FBS) and Penicillin/Steptomycin/L-Glutamine (complete culture medium). Finally, it is stored at 4° C. until its use.

2—Preparation of the Polarised Caco-2 Culture

Coating: 12 hours prior to inoculating the cells, the inserts (6.5 mm diameter transwells) are positioned on the wells of corresponding size, and type 1 rat-tail collagen solution (1 g/L glucose) without serum is applied to the upper face of the polycarbonate filters (0.4 μm pore diameter semi-permeable membranes) of each insert, and it is left at 37° C. in the cell culture stove (90% humidity, 5% $CO_2$). Before its use, the excess coating solution is drawn up from the apical face, it is left for 15 to 30 minutes in the culture stove, and the Caco-2 cells are inoculated at a density of $5 \times 10^5$ cells/cm$^2$. The culture is maintained for 13 days, changing the medium every 48-72 hours, putting 300 μl of complete culture medium in the apical compartment and 900 μl in the basal compartment. On day 13, the barrier state controls (polarisation) of the Caco-2 monolayer are performed by TEER (Trans Epithelial Electric Resistance) and paracellular permeability measurements. These controls allow the functional state of the cell system to be determined as a barrier prior to coating with gelatine.

3—Gelatine Application

It is placed in a culture bath at 37° C. until it is completely liquefied and it is equilibrated at the culture temperature (37° C.). Then, the culture medium is removed from the two compartments of each insert and the culture is washed with culture medium in the 2 compartments of each insert. Next, 300 •1 of liquid gelatine 2.5% is applied on the apical compartment and 900 •1 on the basal compartment, and it is left to solidify for between 2 to 3 hours in the flow hood and at room temperature (20-25° C.).

Once the gelatine has solidified, the plates are sealed with parafilm and they are kept at room temperature until they are used (maximum of 4 days later).

4. Gelatine Elimination

When one wants to use the immobilised culture, the plate is incubated with solid gelatine within a cell incubator, preferably at 37° C., 90% humidity and 5% $CO_2$ for 3 to 4 hours until the gelatine is completely liquefied. Then, it is eliminated from both compartments by suction and the culture is washed with equilibrated culture medium at 37° C. Next, the specific culture medium for Caco-2 cells is applied and the cells are preferably incubated at 37° C., in 90% humidity/5% $CO_2$ until its use (minimum 24 hours; maximum 9 days after), changing the medium every 48-72 hours.

TABLE 1

Stability of the functional barrier state of the Caco-2 cell system, stored in 2.5% gelatine at room temperature, evaluated by TEER measurements (values in ohm × cm$^2$).

| | | IMMOBILISATION TIME IN GELATINE | | | | |
|---|---|---|---|---|---|---|
| | | 1 DAY | 3 DAYS | 4 DAYS | 5 DAYS | 7 DAYS |
| | BEFORE | 3637.81 ± 93.34 | 3027.97 ± 154.55 | 4949.01 ± 140.90 | 4855.51 ± 5.5 | 4855.51 ± 5.5 |
| TIME | 3 DAYS | 3451.89 ± 541.30 | 3117.73 ± 13.10 | 3528.51 ± 198.45 | 1743.17 ± 63.29 | 882.97 ± 563.3 |
| AFTER | 5 DAYS | 3434.53 ± 5.81 | 3143.03 ± 178.6 | ND | ND | ND |
| GELATINE | 9 DAYS | 4110.15 ± 503.74 | 3318.15 ± 267.4 | ND | ND | ND |

(ND: Not determined)

As has been shown in Table 1, only a significant reduction is observed in the TEER values obtained after 5 and 7 days of immobilisation in gelatine, compared with the control values obtained before applying it. This result indicates that the storage method in gelatine disclosed in this invention permits: 1) immobilising the Caco-2 system for up to 4 days at room temperature without affecting its functional barrier state; and 2) once the gelatine has been removed, maintain for up to 9 days after its functional state to perform barrier permeability assays.

Example 2

Characteristics of the Cultures and Determination of the Culture's Lifetimes Before Applying Gelatine Table II indicates some of the cell types which can be cultured in transwell-type supports which form monolayers and which can be stored and transported in gelatine in its barrier state and, therefore, cultures to which the present transport method is applicable.

Caco-2, TC7, HT29 M6: intestinal epithelial lines derived from tumours.

MDCK: kidney epithelial lines
HEK: primary human skin keratinocytes
HUVEC, HMEC-1, BBEC, HAEC, BAEC: primary endothelial cell cultures or lines.

TABLE II

Cell densities recommended for inoculation in inserts and culture times for obtaining in vitro barrier systems.

| Cell type | Cell density/cm$^2$ | Culture time | Recommended insert type | Lifetime in applying gelatine |
|---|---|---|---|---|
| Caco-2 | $5 \times 10^5$ | 21-25 days | 6.5 mm (0.4•m pore) | 13-14 days |
| TC7 | $6 \times 10^4$ | 21-25 days | 6.5 mm (0.4•m pore) | 13-14 days |
| HT29 M6 | $5 \times 10^5$ | 21-25 days | 6.5 mm (0.4•m pore) | 13-14 days |
| MDCK | $8 \times 10^4$ | 6-8 days | 12 mm (0.4•m pore) | ND |
| HEK | $5 \times 10^5$ | 7-8 days | 12 mm (0.4•m pore) | ND |
| HUVEC | $6 - 7 \times 10^4$ | 6-7 days | 12 mm (0.4•m pore) | ND |
| HMEC-1 | $6 - 7 \times 10^4$ | 6-7 days | 12 mm (0.4•m pore) | ND |
| BBEC | $2.5 \times 10^4$ | 11-13 days (with astrocytes) | 24 mm (0.4•m pore) | ND |

(ND: Not determined)

The culture times indicated in Table II relate to the optimal time interval to obtain a polarised monolayer, beyond which it loses its optimum functional properties as cell barrier.

The determination of the lifetimes (moment of the culture wherein the gelatine is applied) of these cell systems, which, in turn, permits preserving its functional barrier state and leaving the user time to perform the assay, has been performed experimentally using TEER and paracellular permeability measurements.

The gelatine is applied to the culture at the point wherein the suitable functional state is reached. In the case of the Caco-2 cell barrier permeability test, the gelatine is preferably applied on day 13 (minimum approximate time wherein the cells begin to form a functional polarised monolayer or barrier). They can be kept in gelatine up to approximately day 17 at room temperature and used up to approximately day 25, without losing their functional barrier properties.

The lifetimes of either other cell types (fibroblasts, tumoral lines) or the same described in Table II but defined for different functional applications of the barrier permeability assay (adhesion assay, migration assay, invasion assay), represent different gelatine application times. Thus, in the specific case of fibroblasts and HUVEC cells inoculated in transwell-type support cells and in conditions wherein these cells are functionally active for a migration assay, the lifetime will be between 30 minutes and 1 hour after inoculating the cells. In the case of an invasion assay, the time will be between 1 and 24 hours.

Example 3

Method of Storing and Transporting Cell Systems for Ready-to-Use Migration/Invasion Assays 1.—Gelatine Preparation Type A pigskin gelatine is used, dissolved in the culture medium corresponding to the cell type which is going to be used (e.g. DMEM (1 g/L glucose) in the case of fibroblasts or EBM medium in the case of HUVEC endothelial cells) at 50° C. and directly at the use concentration (maximum concentration that can be dissolved: 10%). In the present case, 2.5 g of powdered gelatine are weighed and it is dissolved with 100 ml of DMEM culture medium (1 g/L glucose). To increase cell survival during storage and transport, 25 mM HEPES is added to the conditioning medium. It is immediately sterilised (with "heat") by filtration through 0.22 •m pore filters. Then it is supplemented with foetal bovine serum (percentage in accordance with cell type) and Penicillin/Steptomycin/L-Glutamine (complete culture medium). Finally, it is stored at 4° C. until its use.

2.—Preparation of Cell Culture on the Asymmetric Support

In the case of coating, 12 hours before inoculating the cells, the inserts (Fluoroblock system of 3 or 8 μm diameter) are placed on the wells of corresponding size, a solution of the corresponding matrix (collagen, fibronectine, vitronectine, etc) diluted in PBS is applied on the upper and lower face of the fibres of each insert, and it is left at 37° C. in the cell culture stove (90% humidity, 5% $CO^2$). Before its use, the excess coating solution is drawn up from the apical face, and it is left for 15 to 30 minutes in the culture stove, and the cells are inoculated at a density depending on the culture type (between $5 \times 10^0$ and $1^x\ 10^5$ cells/cm$^2$). If the asymmetric support is not coated with matrix, the cells are directly inoculated on the filter. In this type of assay, during the period of cell inoculation and adhesion (between 30 minutes and 1 hour), it is not necessary to put medium in the basal compartment of the Fluoroblock system. The corresponding test is performed with part of the inoculated cells, while gelatine is applied to the rest for their maintenance at room temperature. These controls allow the functional state of the cell system to be determined.

3—Gelatine Application

The gelatine solution is placed in a culture bath at 37° C. until it is completely liquefied and it is equilibrated at the culture temperature (37° C.). Then, the culture medium is removed from the apical compartments of each insert and it is washed with culture medium (without serum in this case). Next, 300 •1 of 2.5% liquid gelatine is applied in the apical compartments, and it is left to solidify for between 2 to 3 hours in the flow hood. Then, 700 •1 is added to the basal compartment, and once solidified in the flow hood, it is stored at room temperature (20-25° C.). Once the gelatine has solidified, the plates are sealed with parafilm and they are kept at room temperature until they are used (maximum of 4 days later).

4.—Gelatine Elimination

When one wants to use the immobilised culture, the plate is incubated with solid gelatine within a cell incubator at 37° C., 90% humidity and 5% $CO_2$ for 3 to 4 hours until the gelatine is completely liquefied. Then, it is eliminated from both compartments by suction and the culture is washed with culture medium without serum equilibrated at 37° C. At this point the culture medium is prepared to perform the migration/invasion assay.

The migration assay (24 h migration) compares the response of HUVEC cells which have not been kept in conditioning medium (without conditioning medium) with the response of HUVEC cells kept for 72 hours with conditioning medium. In both cases, the cells have been stimulated (control +) with complete EBM medium (with growth factors and 10% foetal bovine serum). The non-stimulated cells (control −) have been maintained with EBM without supplement in the basal part.

As has been shown in FIG. 1, the cells maintained in gelatine are capable of responding to a migratory stimulus (control+ in the figure). This result indicates that the storage method in gelatine disclosed in this invention permits: 1) immobilising the HUVEC system for up to 3 days at room temperature without affecting its functional state; and 2) once the gelatine has been removed, a migration test can be performed.

The invention claimed is:

1. A method of storing and/or transporting in vitro organized, differentiated, polarized and functionally active two-dimensional cell cultures, which comprises the following steps:
   a) coating an organized, differentiated, polarized and functionally active two-dimensional cell culture that is immobilized on an asymmetric support with a gelatin solution in the culture medium at a concentration of between 1 and 5%, said cell culture comprising cells in suitable functional state prior to coating,
   b) solidifying the gelatin added to the support at a temperature of between 15 and 25° C., and
   c) storing and/or transporting the cell culture comprising cells in said suitable functional state at a temperature of between 15 and 25° C. for a period of up to 96 hours.

2. A method according to claim 1, which comprises the additional steps:
   a) liquefication of the gelatin,
   b) elimination of the gelatin and substitution thereof by a culture medium, and
   c) incubation of the culture.

3. A method according to claim 2, wherein the cell culture is selected from among: Huvec cells, grown to confluence on a collagen support and differentiated Caco-2 cells, and other types of cells capable of growing in monolayers.

4. A method according to claim 1 wherein said gelatin solution comprises a 2.5% gelatin solution.

5. A method according to claim 1 wherein the gelatin is solidified at a temperature of between 15 and 25° C., for a period of between 30 minutes and 12 hours.

6. A method according to claim 1 wherein the asymmetric support comprises a transwell-type support.

7. A method according to claim 2 wherein the gelatin liquefication is performed between 35 and 40° C. for a period of 1 to 4 hours.

8. A method according to claim 7, wherein the gelatin liquefication is performed at 37° C.

9. A method according to claim 2 wherein the incubation of the culture is performed at between 35 and 40° C. for a period of between 1 hour and 8 days.

10. A method according to claim 9, wherein the incubation of the culture is performed at 37° C.

11. A kit for storing and/or transporting in vitro two-dimensional cell cultures according to claim 1, comprising:
   (i) an asymmetric support, and
   (ii) a gelatin solution in culture medium at a concentration of between 1 and 5%.

12. A kit according to claim 11, wherein the asymmetric support comprises a transwell-type support.

* * * * *